United States Patent [19]

Berg

[11] Patent Number: 5,763,694
[45] Date of Patent: Jun. 9, 1998

[54] SEPARATING 3-METHYL-1-BUTANOL FROM 1-PENTANOL BY AZEOTROPIC DISTILLATION

[76] Inventor: Lloyd Berg, 1314 S. 3rd Ave., Bozeman, Mont. 59715

[21] Appl. No.: 892,523

[22] Filed: Jul. 14, 1997

[51] Int. Cl.⁶ .................................................... C07C 27/30
[52] U.S. Cl. ............................ 568/913; 203/57; 203/44; 203/46; 203/59; 203/60; 203/62; 203/68
[58] Field of Search .............................. 568/913; 203/57, 203/60, 62, 68, 59, 44, 46

[56] References Cited

U.S. PATENT DOCUMENTS 5,439,561  8/1995  Berg .......................................... 203/58

*Primary Examiner*—Gary Geist
*Assistant Examiner*—Jean F. Vollano

[57] ABSTRACT

3-Methyl-1-butanol cannot be separated from 1-pentanol by distillation or rectification because of the closeness of their boiling points. 3-Methyl-1-butanol is readily separated from 1-pentanol by azeotropic distillation. Effective agents are methylcyclohexane, methyl formate and tetrahydrofuran.

1 Claim, No Drawings

SEPARATING 3-METHYL-1-BUTANOL FROM 1-PENTANOL BY AZEOTROPIC DISTILLATION

FIELD OF THE INVENTION

This invention relates to a method of separating 3-methyl-1-butanol from 1-pentanol by azeotropic distillation.

DESCRIPTION OF PRIOR ART

Azeotropic distillation is the method of separating close boiling compounds or azeotrones from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectifications.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 100 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

3-Methyl 1-butanol and 1-pentanol boil 8 degrees apart and have a relative volatility of 1.05 which makes it impossible to separate them by conventional distillation or rectification. Table 2 shows that with an agent giving a relative volatility of 1.4 only 35, actual plates are required to get 99% purity.

TABLE 2

Theoretical and Actual Plates Required vs. Relative Volatilty for 3-Methyl-1-butanol from 1-Pentanol Separation

| Relative Volatility | Theoretical Plates Required At Total Reflux, 99% Purity | Actual Plates Required, 75% Eff. |
|---|---|---|
| 1.3 | 34 | 46 |
| 1.4 | 26 | 35 |

OBJECTIVE OF THE INVENTION

The object of this invention is to provide a process or method of azeotropic distillation that will enhance the relative volatility of 3-methyl-1-butanol and 1-pentanol in their separation in a rectification column. It is a further object of this invention to identify effective azeotropic distillation agents that are stable and can be recycled.

SUMMARY OF THE INVENTION

The objects of this invention are provided by a process for the separation of 3-methyl-1-butanol and 1-pentanol which entails the use of certain organic compounds when employed as the agent in azeotropic distillation.

TABLE 3

Effective Azeotropic Distillation Agents For Separating 3-Methyl-1-Butanol From 1-Pentanol

| Compounds | Relative Volatility |
|---|---|
| None | 1.05 |
| Methyl acetate | 1.35 |
| Dimethyl carbonate | 1.4 |
| Methyl formate | 1.5 |
| Methyl butyrate | 1.4 |
| Methyl propionate | 1.38 |
| Ethyl propionate | 1.35 |
| Butyl propionate | 1.38 |
| Acetone | 1.45 |
| 2-Butanone | 1.48 |
| 3-Pentanone | 1.35 |
| Isopropyl acetate | 1.35 |
| 2-Pentanone | 1.35 |
| 4-Methyl-2-pentanone | 1.43 |
| Ethyl formate | 1.45 |
| Benzene | 1.37 |
| Cyclohexane | 1.35 |
| Cyclohexene | 1.35 |
| Hexane | 1.42 |
| p-Xylene | 1.35 |
| 1-Octene | 1.42 |
| Octane | 1.35 |
| Isooctane | 1.35 |
| 2,2,4-Trimethylpentane | 1.5 |
| Ethyl ether | 1.35 |
| Petroleum ether | 1.4 |
| Isopropyl ether | 1.4 |
| Ethylene glycol dimethyl ether | 1.35 |
| Dioxolane | 1.37 |
| Dimethoxymethane | 1.45 |
| Butyraldehyde | 1.4 |
| Acetol | 1.35 |
| Dipropyl amine | 1.35 |
| Triethyl amine | 1.35 |
| Nitroethane | 1.37 |
| Tetrahydrofuran | 1.43 |
| Methylcyclohexane | 1.45 |
| Ethyl benzene | 1.38 |
| Ethyl acetate | 1.4 |
| 1,4-Dioxane | 1.35 |

DETAILED DESCRIPTION OF THE INVENTION

I have discovered that certain organic compounds will effectively increase the relative volatility between 3-methyl-1-butanol and 1-pentanol during rectification when employed as the agent in azeotropic distillation. They are methyl acetate, dimethyl carbonate, methyl formate, methyl butyrate, methyl propionate, ethyl propionate, butyl pronionate, acetone, 2-butanone, 3-pentanone, isopropyl acetate, 2-pentanone, 4-methyl-2-pentanone, ethyl formate, benzene, cyclohexane, cyclohexene, hexane, p-xylene, 1-octene, octane, isooctane, 2,2,4-trimethylpentane, ethyl ether, petroleum ether, isopropyl ether, ethylene glycol dimethyl ether, dioxolane, dimethoxymethane, butyraldehyde, acetol, dipropyl amine, triethyl amine, nitroethane, tetrahydofuran, methylcyclohexane, ethyl benzene, ethyl acetate and 1,4-dioxane.

THE USEFULNESS OF THE INVENTION

The usefulness of this invention can be demonstrated by referring to the data presented in Tables 1, 2 and 3. All of the successful agents show that 3-methyl-1-butanol can be separated from 1-pentanol by means of azeotropic distillation in a rectification column and that the ease of separation as measured by relative volatility is considerable.

WORKING EXAMPLE

1. Fifty grams of 3-methyl-1-butanol-1-pentanol mixture and fifty grams of methylcyclohexane were charged to a vapor-liquid equilibrium still and refluxed for four hours. The vapor composition was 84.3% 3-methyl-1-butanol and 15.7% 1-pentanol; the liquid composition was 79% 3-methyl-1-butanol and 21% 1-pentanol. This is a relative volatility of 1.43.

I claim:

1. A method for recovering 3-methyl-1-butanol from a mixture of 3-methyl-1-butanol and 1-pentanol which comprises distilling a mixture of 3-methyl-1-butanol and 1-pentanol in the presence of an azeotrope forming agent, recovering the 3-methyl-1-butanol and the azeotrope forming agent as overhead product and obtaining the 1-pentanol as bottoms product, wherein said azeotrope forming agent consists essentially of one material selected from the group consisting of methyl acetate, dimethyl carbonate, methyl formate, methyl butyrate, methyl propionate, ethyl propionate, butyl propionate, acetone, 2-butanone, 3-pentanone, isopropyl acetate, 2-pentanone, 4-methyl-2-pentanone, ethyl formate, benzene, cyclohexane, cyclohexene, hexane, p-xylene, 1-octene, octane, isooctane, 2,2,4-trimethylpentane, petroleum ether, isopropyl ether, ethylene glycol dimethyl ether, dioxolane, butyraldehyde, acetol, dipropyl amine, triethyl amine, nitroethane, tetrahydrofuran, methylcyclohexane, ethyl benzene, and 1,4-dioxane.

* * * * *